United States Patent [19]

Lederis et al.

[11] Patent Number: 4,528,189
[45] Date of Patent: Jul. 9, 1985

[54] UROTENSIN PEPTIDES

[75] Inventors: Karl P. Lederis; Keith L. MacCannell, both of Calgary, Canada; Jean E. F. Rivier, LaJolla, Calif.

[73] Assignee: The Salk Institute For Biological Studies, San Diego, Calif.

[21] Appl. No.: 463,397

[22] Filed: Feb. 3, 1983

[51] Int. Cl.$^3$ .................... C07C 103/52; A61K 37/02
[52] U.S. Cl. ................................ 514/12; 260/112.5 R
[58] Field of Search .................. 260/112.5 R; 424/177

[56] References Cited

U.S. PATENT DOCUMENTS 4,385,050  5/1983  Lederis et al. ...................... 424/177

OTHER PUBLICATIONS

Lederis et al., *Endocrine Society Meeting*, 64th Annual Meeting, Jun. 16–18, 1982, abst. A756.
Lederis et al., *Proceedings of the Western Pharmacological Society*, vol. 25, 1982, pp. 223–227.
Lederis et al., *Science*, 218, No. 4568, 162–164, (Oct. 8, 1982).

*Primary Examiner*—Delbert R. Phillips
*Assistant Examiner*—F. T. Moezie
*Attorney, Agent, or Firm*—Fitch, Even, Tabin & Flannery

[57] ABSTRACT

UI (Urotensin I) or white sucker urotensin, obtained from *Catostomus commersoni*, has the formula: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-NH$_2$. Analogs have been synthesized that are at least as potent as UI, and UI or such an analog or a fragment of either or a pharmaceutically acceptable salts of any of the foregoing, dispersed in a pharmaceutically acceptable liquid or solid carrier, can be administered to mammals to achieve a substantial elevation of ACTH, $\beta$-endorphin, $\beta$-lipotropin and corticosterone levels and/or an increase in intestinal blood flow and/or a lowering of systemic blood pressure and/or a changing of regional blood distribution over an extended period of time. In the analogs, one or more of the first three N-terminal residues is deleted and substituted by a peptide fragment up to 5 amino acids long and/or an acylating agent containing up to 7 carbon atoms is added at the N-terminal.

11 Claims, No Drawings

UROTENSIN PEPTIDES

This invention was made with Government support under Grant No. AM-26741 awarded by the National Institutes of Health (DHHS). The Government has certain rights in this invention.

This invention is directed to peptides related to Urotensin I (UI) and to methods for pharmaceutical treatment of mammals using such peptides. More specifically, the invention relates to UI and analogs of UI, to pharmaceutical compositions containing UI or its analogs and to methods of treatment of mammals using UI or its analogs.

BACKGROUND OF THE INVENTION

Experimental and clinical observations have supported the concept that the hypothalamus plays a key role in the regulation of adenohypophysial corticotropic cells secretory functions. Over 25 years ago, Guillemin, Rosenberg and Saffran and Schally independently demonstrated the presence of factors in hypothalamus which would increase the rate of ACTH secretion by the pituitary gland incubated in vitro or maintained in an organ culture. A physiologic corticotrop regulatory factor, CRF, was extracted from sheep hypothalamic fragments and characterized and synthesized by the Peptide Biology Laboratory at The Salk Institute, as described in Vale et al., *Science* 213:1394–1397, 1981.

Sauvagine is a 40-residue, amidated generally similar peptide, which was isolated from the skin of the South American frog *Phyllomedusa sauvagei*, was characterized by Erspamer et al. and was described in *Regulatory Peptides*, Vol. 2 (1981), pp. 1–13. Sauvagine has the formula: pGlu-Gly-Pro-Pro-Ile-Ser-Ile-Asp-Leu-Ser-Leu-Glu-Leu-Leu-Arg-Lys-Met-Ile-Glu-Ile-Glu-Lys-Gln-Glu-Lys-Glu-Lys-Gln-Gln-Ala-Ala-Asn-Asn-Arg-Leu-Leu-Leu-Asp-Thr-Ile-NH$_2$. Sauvagine has been reported to have biological activity in lowering blood pressure in mammals and in stimulating the secretion of ACTH and $\beta$-endorphin.

SUMMARY OF THE INVENTION

UI has now been isolated from urophyses of *Catostomus commersoni*(white sucker), purified and characterized as a polypeptide having the formula: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-NH$_2$. It may alternatively be referred to as white sucker urotensin. The purification and characterization are described in an article by Lederis et al., *Science* Vol. 218, No. 4568, 162–164 (Oct. 8, 1982). The syntheses of the 41-residue peptide and the 38-residue fragment (UI 4-41) have been completed, and both synthetic UI and its fragment have been found to stimulate ACTH and $\beta$-endorphin activies in vitro and in vivo and to substantially lower blood presssure for an extended time period. UI in substantially pure form (i.e. substantially free of the remainder of a crude biological extract or of related synthetic replicates) can be employed in pharmaceutical compositions, and a purity of at least about 93% or higher (based upon other peptides present) is practically obtainable and preferred for clinical testing.

Analogs of white sucker urotensin having the following formula have at least substantially the same biological activity: Y-R$_1$-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-NH$_2$ wherein Y is an acyl group having 7 or less carbon and R$_1$ is a peptide fragment up to 5 residues long or is des-R$_1$.

Pharmaceutical compositions in accordance with the invention include synthetic UI or its analogs or the biologically active fragments of either, or nontoxic addition salts thereof, dispersed in a pharmaceutically acceptable liquid or solid carrier. The administration of such peptides or pharmaceutically acceptable addition salts thereof to mammals in accordance with the invention may be carried out for the regulation of secretion of ACTH, $\beta$-endorphin, $\beta$-lipotropin, and corticosterone and/or for the long-lasting lowering of systemic blood pressure and/or changing of regional blood distribution and/or increasing mesenteric flow and/or for affecting mood, behavioral and gastrointestinal functions.

DETAILED DESCRIPTION OF THE PREFERRED EMBODIMENTS

UI was isolated from urophysis extracts of the teleost, *Catostomus commersoni*(white sucker), purified and characterized; urophyses are the hormone storage-release organs of the caudal neurosecretory system. The nomenclature used to define the peptides is that specified by Schroder & Lubke, "The Peptides", Academic Press (1965) wherein, in accordance with conventional representation, the amino group appears to the left and the carboxyl group to the right. Where the amino acid residue has isomeric forms, it is the L-form of the amino acid that is represented unless otherwise expressly indicated.

The invention provides UI analogs having the following formula: Y-R$_1$-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-NH$_2$ wherein Y is an acyl group having 7 or less carbon atoms or hydrogen and R$_1$ is a peptide fragment up to 5 residues long or is des-R$_1$. Preferably R$_1$ is Asn-Asp-Asp or Asp-Asp or Asp.

The peptides are synthesized by a suitable method, such as by exclusively solid-phase techniques, by partial solid-phase techniques, by fragment condensation or by classical solution addition. UI and certain fragments may also be synthesized by recently developed recombinant DNA techniques.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Also considered to be within the scope of the present invention are intermediates of the formula: X$^1$-R$_1$(X)-Pro-Pro-Ile-Ser(X$^2$)-Ile-Asp(X$^5$)-Leu-Thr(X$^2$)-Phe-His(X$^7$)-Leu-Leu-Arg(X$^3$)-Asn(X$^4$)-Met ($X^8$)-Ile-Glu($X^5$)-Met($X^8$)-Ala-Arg($X^3$)-Ile-Glu($X^5$)-Asn($X^4$)-Glu($X^5$)-Arg($X^3$)-Glu($X^5$)-Gln($X^4$)-Ala-Gly-Leu-Asn($X^4$)-Arg($X^3$)-Lys($X^6$)-Tyr($X^9$)-Leu-Asp($X^5$)-Glu($X^5$)-Val-$X^{10}$ wherein: the $R_1$ is as hereinbefore defined; $X^1$ is either hydrogen or an α-amino protecting group. The α-amino protecting groups contemplated by $X^1$ are those known to be useful in the art in the step-wise synthesis of polypeptides. Among the classes of α-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; and (5) thiourethan-type protecting groups, such as phenylthiocarbonyl. The preferred α-amino protecting group is BOC.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg preferably selected from the class consisting of nitro, p-toluenesulfonyl(Tos), Z, adamantyloxycarbonyl and BOC, or is hydrogen. Tos is most preferred.

$X^4$ is hydrogen or a protecting group for the amido group of Asn or Gln and is preferably xanthyl(Xan).

$X^5$ is hydrogen or an ester-forming protecting group for the β- or γ-carboxyl group of Asp or Glu, preferably selected from the class consisting of benzyl (OBzl), 2,6-dichlorobenzyl, methyl, ethyl and t-butyl esters. OBzl is most preferred.

$X^6$ is hydrogen or a protecting group for the side chain ε-amino substituent of Lys. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore.

$X^7$ is hydrogen or a protecting group for the imidazole nitrogen of His, such as Tos or 2,4-dinitrophenyl(DNP).

$X^8$ is hydrogen or a protecting group for the sulfur of Met, such as oxygen.

$X^9$ is hydrogen or a protecting group for the hydroxyl group of Tyr, such as DCB, p-methoxybenzyl or Bzl, with DCB being preferred.

X is hydrogen or a protecting group or groups for a labile side chain of one or more amino acid residues comprising $R_1$.

The selection of a side chain amino protecting group is not critical except that it should generally be one which is not removed during deprotection of the α-amino groups during the synthesis. Hence, the α-amino protecting group and the side chain amino protecting group cannot be the same. Xan is an exception however; as once coupling is complete, further protection of the amido group is not of prime importance.

$X^{10}$ is selected from the class consisting of NH$_2$, carboxyl protecting groups which can be cleaved under conditions that do not cleave the $X^5$ group, and an anchoring bond used in solid phase synthesis for linking to a solid resin support, preferably one represented by the formulae: -O-CH$_2$-benzyl-polyamide resin support, -NH-benzhydrylamine (BHA) resin support, and -NH-paramethylbenzhydrylamine (MBHA) resin support. The polyamide polymer is commercially available and is discussed in detail in *Bioorganic Chemistry*, 8, 351-370 (1979) where a preferred version of it is discussed in connection with the synthesis illustrated in FIG. 6. When it is employed, the side-chain-protecting groups may first be cleaved by hydrogen fluoride (HF) treatment, and the peptide may subsequently be cleaved from the resin as the amide by ammonolysis. Use of BHA or MBHA resin is preferred, and cleavage directly gives the UI amide or UI fragment amide.

In the formula for the intermediate, at least one of X, $X^1$, $X^2$, $X^3$, $X^4$, $X^5$, $X^6$, $X^7$, $X^8$, $X^9$ and $X^{10}$ is a protecting group or an anchoring bond. In selecting a particular side chain protecting group to be used in the synthesis of the peptides, the following rules are followed: (a) the protecting group must retain its protecting properties and not be split off under coupling conditions, (b) the side-chain protecting group must be stable to the deblocking reagent and with the exception of Xan, should also be stable under the reaction conditions selected for removing the α-amino protecting group at each step of the synthesis, and (c) the side-chain-protecting group must be removable, upon the completion of the synthesis of the desired amino acid sequence, under reaction conditions that will not alter the peptide chain. When $X^{10}$ is a protecting group at the C-terminal, it should be chosen so that it can be cleaved under conditions which will not also cleave the $X^5$ protecting group for the side-chain-carboxyl group of Asp or Glu, e.g. $X^{10}$ may be BHA or MBHA when $X^5$ is OBzl or $X^{10}$ may be OBzl when $X^5$ is t-butyl ester or H. This allows the C-terminus to be deprotected and amidated upon completion of the synthesis (by classical methods, fragment condensation or a combination thereof) without amidating the side-chain carboxyl groups, which are subsequently deprotected, except of course in the case where $X^5$ is H.

For the acyl group represented by Y, acetyl (Ac), formyl, acrylyl and benzoyl are preferred. For the 1 to 5 amino acid peptide which may be optionally included without adversely affecting the potency, any amino acids may be used, but the L- or D- forms of the naturally occurring, protein-derived amino acids would normally be used.

The peptides are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminal end of the peptide by coupling a protected α-amino to a suitable resin as generally set forth in U.S. Pat. No. 4,244,946 issued Jan. 21, 1981 to Rivier et al., the disclosure of which is incorporated herein by reference. Such a starting material for UI peptides can be prepared by attaching α-amino-protected Val to an MBHA resin.

Val protected by BOC is coupled to the BHA resin using methylene chloride and dimethylformamide (DMF). Following the coupling of BOC-Val to the resin support, the α-amino protecting group is removed, as by using trifluoroacetic acid(TFA) in methylene chloride, TFA alone or with HCl in dioxane. Preferably 50 weight % TFA in methylene chloride is used with 1-5 weight % 1,2 ethanedithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72-75 (Academic Press 1965).

After removal of the α-amino protecting group of Val, the remaining α-amino- and side chain-protected amino acids are coupled stepwise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1-27 (1970).

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp. 1927-1938.

After the desired amino acid sequence has been completed, the intermediate peptide is removed from the resin support by treatment with a reagent, such as liquid hydrogen fluoride. Selection of all of the protecting groups is preferably such that HF treatment not only cleaves the peptide from the resin but also cleaves all remaining side chain protecting groups X, $X^2$, $X^3$, $X^4$, $X^5$, $X^6$, $X^7$, $X^8$ and $X^9$ and the α-amino protecting group $X^1$ (unless it is an acyl group which is intended to be present in the final peptide), to obtain the peptide. When using hydrogen fluoride for cleaving, anisole and methylethyl sulfide are included in the reaction vessel as scavengers. Because Met is present in the sequence, the preferred BOC protecting group for the α-amino group is preferably cleaved with trifluoroacetic acid(TFA)/ethanedithiol prior to cleaving the peptide from the resin to eliminate S-alkylation.

The following Example sets forth the preferred method for synthesizing UI by the solid-phase technique.

EXAMPLE I

The synthesis of the UI having the formula: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-$NH_2$ is conducted in a stepwise manner on a paramethyl-benzhydrylamine hydrochloride resin, such as available from Bachem, Inc., having a substitution range of about 0.1 to 0.5 mmoles/gm. resin. The synthesis is performed on an automatic Beckman 990A peptide synthesizer. Coupling of BOC-Val results in the substitution of about 0.35 mmol. Val per gram of resin. All solvents that are used are carefully degassed, preferably by sparging with an inert gas, e.g. helium or nitrogen, to insure the absence of oxygen that might undesirably oxidize the sulfur of the Met residue.

After deprotection and neutralization, the peptide chain is built step-by-step on the resin. Generally, one to two mmol. of BOC-protected amino acid in methylene chloride is used per gram of resin, plus one equivalent of 1 molar DCCI in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) is used to activate the carboxyl end of Asn or Gln, and for example, BOC-Asn(ONp) is coupled overnight using one equivalent of HOBt in a 50% mixture of DMF and methylene chloride. The amido group of Asn or Gln is protected by Xan when DCC coupling is used instead of the active ester method. 2-Cl-Z is used as the protecting group for the Lys side chain, and Tyr is protected by DCB. Tos is used to protect the guanidino group of Arg and the imidazole group of His, and the side chain carboxyl group of Glu or Asp is protected by OBzl. Met is left unprotected. At the end of the synthesis, the following composition is obtained BOC-Asn(Xan)-Asp(OBzl)-Asp(OBzl)-Pro-Pro-Ile-Ser(Bzl)-Ile-Asp(OBzl)-Leu-Thr(Bzl)-Phe-His(Tos)-Leu-Leu-Arg(Tos)-Asn(Xan)-Met-Ile-Glu(OBzl)-Met-Ala-Arg(Tos)-Ile-Glu(OBzl)-Asn(Xan)-Glu(OBzl)-Arg(Tos)-Glu(OBzl)-Gln(Xan)-Ala-Gly-Leu-Asn(Xan)-Arg(Tos)-Lys(2-Cl-Z)-Tyr(DCB)-Leu-Asp(OBzl)-Glu(OBzl)-Val-resin support. Xan may have been partially or totally removed by TFA treatment used to deblock the alpha-amino protecting group.

In order to cleave and deprotect the resulting protected peptide-resin, it is treated with 1.5 ml. anisole, 0.5 ml. of methyl ethyl sulfide and 15 ml. hydrogen fluoride (HF) per gram of peptide-resin, first at $-20°$ C. for 20 min. and then at 0° C. for one-half hour. After elimination of the HF under high vacuum, the resin-peptide is washed alternately with dry diethyl ether and chloroform, and the peptide is then extracted with de-gassed 2N aqueous acetic acid and separated from the resin by filtration.

The peptide is purified by gel permeation followed by semi-preparative HPLC as described in Rivier et al., *Peptides: Structure and Biological Function* (1979) pp. 125-128, or by preparative HPLC for large-scale production.

Specific optical rotation of the urotensin peptide, which was synthesized and purified in the foregoing manner, was measured on a Perkin Elmer Model 141 as $[\alpha]_D^{22} = -62.4° \pm 1.0$ (c=1 in 1% acetic acid) (without correcting for the presence of $H_2O$ and TFA) and had a purity of about 96%.

To produce the fragment sucker UI (4-41), a portion of the purified peptide is subjected to mild acid hydrolysis. To check whether the precise sequence was achieved following synthesis and acid hydrolysis, the peptide was hydrolyzed in sealed evacuated tubes containing 6N HCl for 20 hours at 110° C. Amino acid analyses of the hydrolysates using a Beckman 121 MB amino acid analyzer showed the following amino acid ratios: Asx(5.23), Thr(1.04), Ser(0.96), Glx(5.63), Pro(2.04), Gly(1.06), Ala(2.02), Val(1.00), Met(2.04), Ile(4.04), Leu(5.23), Tyr(0.96), Phe(1.00), Lys(1.00), His(1.04) and Arg(4.15), which confirmed that the 38-residue peptide structure had been obtained.

EXAMPLE II

UI was extracted, isolated and purified in the following manner. About 2,000 urophyses dissected from *Catostomus commersoni* were dehydrated in acetone (yielding about 500 mg.) and homogenized in 0.1N HCl, heated for 15 minutes in a boiling water bath, centrifuged at 3,000 rpm for 20 minutes, and the supernatant was analyzed by gel exclusion chromatography on a Biogel P-6 column (2.6×85 cm) using 0.1N HCl as eluant. Bioactive fractions were pooled and further purified by ion exchange chromatography on a sulfopropyl(SP)-Sephadex C-25 column (1.6×50 cm) using a linear pyridine acetate gradient at 4° C. The gradient was initiated with 0.2M pyridine pH 4.5 gradually changed to 2.0M pyridine, pH 6.5. Bioactive fractions were again pooled, lyophilized and aliquots were further purified by reverse phase HPLC on a Spectra-Physics SP 8000 liquid chromatograph equipped with a 25 cm×0.46 cm column of Lichrosorb $C_8$, 10 μm (Brownlee Lab) with a linear 19-min gradient of 10–55% acetonitrile in 0.2M ammonium acetate buffer, pH 4.0, at a flow rate of 1.5 ml/min and about 40° C.

UI activity in the fractions was measured by the isolated rat hind limb assay, Lederis, K. et al. "Effects and Assay of Urotensin I on the Perfused Hind Limb of the Rat." *Gen Comp Endocrinol.* 24:10–16, 1974. In vivo hypotensive activity of extracted peptides or those obtained by enzymatic cleavage was measured in anaesthetized rats, Lederis, K. et al. "Pharmacological Observations on the Hypotensive Action of Extracts of Teleost Fish Urophyses (Urotensin I) in the Rat", *Br. J. Pharmac.* 51:315–324, 1974.

Lyophilized active zones from the HPLC were used for composition and completion of structural analysis which gave the following sequence: H-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-$NH_2$.

EXAMPLE III

The procedure of Example II was repeated, leaving out the step of heating in 0.1N HCl using the boiling water bath and instead extracting for a longer period of time in cold 0.1N HCl.

Lyophilized active zones from the HPLC were used for composition and completion of structural analysis which gave the following 41-residue sequence which is sucker UI: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-$NH_2$.

EXAMPLE IV

The urotensin peptides from Examples II and III are examined for effects on the secretion of ACTH and β-endorphin in vitro and also examined in vivo. A high potency of these two peptides to stimulate the secretion of ACTH and β-endorphin by cultured rat pituitary cells is observed, substantially indistinguishable from each other and comparable to amunine (CRF). The peptides also stimulate ACTH and β-END-LI secretion in vivo in several rat preparations. UI activity of the peptides was measured by the isolated rat hind limb assay, Lederis, K. et al. "Effects and Assay of Urotensin I on the Perfused Hind Limb of the Rat", *Gen. Comp. Endocrinol.*, 24:10–16, 1974. In vivo hypotensive activity of extracted peptides was measured in anaesthetized rats, Lederis, K. and Medakovic, M. "Pharmacological Observations on the Hypotensive Action of Extracts of Teleost Fish Urophyses (Urotensin I) in the Rat", *Br. J. Pharmacol.* 51:315–324, 1974, and in anaesthetized dogs, MacCannell and Lederis, "Dilatation of the Mesenteric Vascular Bed of the Dog Produced by a Peptide, Urotensin I", *J. Pharm. Exp. Ther.* 203:38–46, 1977. In the dog and monkey, both peptides, urotensin I and urotensin I (4-41) produce a modest but sustained depression of the blood pressure which appears to be due solely to dilatation of the mesenteric vascular bed; neither peptide dilates other vascular beds and thus change in the regional blood distribution occurs. Both peptides also cause a more marked fall in blood pressure in the rat, where vascular dilatation appears to be less selective. The peptides are several times more potent than amunine in stimulating the secretion of ACTH by teleost fish pituitaries.

In the pentobarbital-anaesthetized dog, the threshold dose of UI for mesenteric vasodilatation, when given close arterially into the cephalic mesenteric A, is between 0.001 and 0.01 μg for both sucker UI (1-41) and for the 4-41 fragment of sucker UI. Doses of 0.1–0.5 μg of both peptides produce a 50–150% increase in mesenteric flow; accompanying changes in blood pressure are very modest (about 10% decrease). The two synthetic peptides described above with respect to Example I have been found to be equipotent with the extracted and purified peptides, as tested in the anaesthetized dog in vivo and in the isolated rat hind limb, as described above, as well as when tested in isolated mesenteric artery strips of the rat according to Muramatsu, I., Miura, A., Fujiwara, M. and Lederis, K., *Gen. Comp. Endocrinol.* 45:446–452, 1981. Comparison of the two extracted and the two synthetic sucker peptides indicate that synthetic UI(1-41) have 111±16% activity and synthetic UI (4-41) have 123±14% activity, relative to the activity of the respective extracted sucker UI peptides.

EXAMPLE V

The peptide having the formula: Ac-Ala-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-$NH_2$ is synthesized. Testing in accordance with the general procedure set forth in Example III shows that it likewise stimulates the secretion of ACTH and β-END-LI and causes vasodilatory-hypotensive activity, including a very significant increasing of mesenteric blood flow and lowering of systemic blood pressure.

EXAMPLE VI

The peptide having the formula: H-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-NH$_2$ is synthesized. Testing in accordance with the general procedure set forth in Example III shows that it has significant mammalian vasodilatory-hypotensive activity, including the increasing of mesenteric blood flow and lowering of systemic blood pressure.

Sucker UI and its biologically active fragments are expected to be very useful in the following clinical conditions:

(a) mesenteric ischemia (ischemic bowel syndrome, ischemic intestinal ulceration, ischemic colitis, ischemic proctitis, nonocclusive mesenteric vascular ischemia, intestinal angina, and mesenteric angina vasculitis) as well as other situations where the blood supply to the intestine is compromised;

(b) anastomotic gut surgery—to increase blood supply to the suture line and thus promote healing;

(c) shock and hypotension, such as may occur with trauma, hemorrhage, fluid loss, infection or may be due to cardiac causes—there being reasonable evidence that decreased intestinal blood flow is involved in the genesis or maintenance of all types of hypotension and shock; and (d) heart failure and other cardiac conditions where a reduction in the "load" against which the heart has to pump is desirable, sometimes termed afterload reduction. (Existing vasodilator drugs may excessively decrease filling of the heart so that cardiac output falls, whereas a selective mesentric vasodilator drug would not.)

Sucker UI is also expected to be of value in the following clinical conditions: inflammatory bowel disease, such as Crohn's (regional ileitis and granulomatous colitis), and ulcerative colitis; and hypertension from various causes, including portal hypertension, which is commonly treated by administration of vasopressin, which is released endogenously by these UI peptides.

If these UI peptides gain access to the brain, they should have significant effects on the brain as a mediator or limiter of the body's stress response—ACTH and β-END secretion being a "sine qua non" of an animal's response. Because they elevate the levels of ACTH and β-END, administration can be used to induce their effects on the brain and its periphery to thereby influence memory, mood, pain appreciation, etc., and more specifically, alertness, depression and/or anxiety.

UI or an analog or a fragment of either, or nontoxic addition salts of the foregoing, combined with a pharmaceutically acceptable carrier to form a pharmaceutical composition, may be administered to mammals, including humans, either intravenously, subcutaneously, intramuscularly, percutaneously, intracerebrospinally or even orally (when suitable oral carriers are developed). The peptides should be at least about 93% pure and preferably should have a purity of at least about 98%. This purity means that the intended peptide constitutes the stated weight % of all like peptides and peptide fragments present. Their administration may be employed by a physician to lower blood pressure or to alter regional blood flow, and the required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, pamoate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. Usually, the dosage will be from about 0.01 to about 200 micrograms of the peptide per kilogram of the body weight of the host. In some instances, treatment of subjects with these peptides can be carried out in lieu of the administration of ACTH or corticosteroids, and in such instances, a dosage as low as about 10 ng/Kg of body weight may be employed. As used herein all temperatures are °C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications in the UI peptide chain can be made in accordance with present or future developments without detracting from the potency, and such resultant peptides are considered as being within the scope of the invention.

Various features of the invention are emphasized in the claims which follow.

What is claimed is:

1. A pharmaceutical composition for lowering blood pressure in mammals or for changing regional blood distribution comprising an effective amount of synthetic UI having the formula: Y-R$_1$-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-NH$_2$ wherein Y is an acyl group having 7 or less carbon atoms or hydrogen and R$_1$ is Asn-Asp-Asp, Asp-Asp, Asp, Ala, or des-R$_1$, or a nontoxic addition salt thereof; and a pharmaceutically acceptable liquid or solid carrier therefor.

2. The composition of claim 1 wherein R$_1$ is Asn-Asp-Asp.

3. A method for increasing intestinal blood flow and/or lowering the blood pressure of a mammal, which method comprises administering to said mammal an effective amount of a pharmaceutical composition as set forth in claim 1.

4. A method in accordance with claim 3 wherein said administering is carried out either intravenously, subcutaneously, percutaneously, intracerebrospinally or intramuscularly.

5. A synthetic polypeptide having the formula: Y-$R_1$-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-$NH_2$, wherein Y is an acyl group having 7 or less carbon atoms or hydrogen and $R_1$ is Asn-Asp-Asp, Asp-Asp, Asp, Ala, or des-$R_1$; or a nontoxic addition salt thereof.

6. The compound of claim 5 wherein $R_1$ is Asn-Asp-Asp.

7. The compound of claim 5 wherein $R_1$ is Asp-Asp.

8. The compound of claim 5 wherein $R_1$ is Asp.

9. A method of elevating the secretion of ACTH and corticosteroids which comprises administering an effective amount of the compound of claim 5.

10. A method of elevating the secretion of beta-endorphine-like secretions, which comprises administering an effective amount of the compound of claim 5.

11. The compound of claim 5 wherein X is Ac and $R_1$ is Ala.

* * * * *